(12) United States Patent
Silver

(10) Patent No.: US 10,434,082 B2
(45) Date of Patent: *Oct. 8, 2019

(54) ISOTHIOCYANATE FUNCTIONAL COMPOUNDS AUGMENTED WITH SECONDARY ANTINEOPLASTIC MEDICAMENTS AND ASSOCIATED METHODS FOR TREATING NEOPLASMS

(71) Applicant: Michael E. Silver, Lake City, MI (US)

(72) Inventor: Michael E. Silver, Lake City, MI (US)

(73) Assignee: The William M. Yarbrough Foundation, Peoria, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/215,753

(22) Filed: Dec. 11, 2018

(65) Prior Publication Data

US 2019/0111018 A1 Apr. 18, 2019

Related U.S. Application Data

(63) Continuation-in-part of application No. 16/025,640, filed on Jul. 2, 2018, now Pat. No. 10,335,387, which is a continuation-in-part of application No. 15/838,444, filed on Dec. 12, 2017, now Pat. No. 10,111,852, which is a continuation of application No. 15/423,869, filed on Feb. 3, 2017, now Pat. No. 9,839,621, which is a continuation-in-part of application No. 14/867,626, filed on Sep. 28, 2015, now Pat. No. 9,642,827, which is a continuation of application No. 14/867,585, filed on Sep. 28, 2015, now Pat. No. 9,636,320, which is a continuation of application No. 14/519,510, filed on Oct. 21, 2014, now Pat. No. 9,504,667, which is a continuation of application No. 13/952,236, filed on Jul. 26, 2013, now Pat. No. 8,865,772.

(60) Provisional application No. 61/676,093, filed on Jul. 26, 2012.

(51) Int. Cl.
| | |
|---|---|
| *A61K 31/26* | (2006.01) |
| *A61K 31/195* | (2006.01) |
| *A61K 31/16* | (2006.01) |
| *A61P 35/00* | (2006.01) |
| *A61K 31/198* | (2006.01) |
| *A61K 9/00* | (2006.01) |

(52) U.S. Cl.
CPC ............ *A61K 31/26* (2013.01); *A61K 9/0014* (2013.01); *A61K 31/16* (2013.01); *A61K 31/195* (2013.01); *A61K 31/198* (2013.01); *A61P 35/00* (2018.01)

(58) Field of Classification Search
CPC ....... A61K 31/26; A61K 31/195; A61K 31/16
USPC ....................................... 514/562, 629, 638
See application file for complete search history.

(56) References Cited

U.S. PATENT DOCUMENTS

| | | |
|---|---|---|
| 2,905,701 A | 9/1959 | Nutting et al. |
| 3,108,040 A | 10/1963 | Folkers |
| 3,725,030 A | 4/1973 | Newallis et al. |
| 3,740,435 A | 6/1973 | Newallis et al. |
| 3,969,087 A | 7/1976 | Saito et al. |
| 4,083,836 A | 4/1978 | Anjou et al. |
| 4,158,656 A | 6/1979 | Jones et al. |
| 4,191,752 A | 3/1980 | Kada et al. |
| 4,938,949 A | 7/1990 | Borch et al. |
| 5,114,969 A | 5/1992 | Chung et al. |
| 5,126,129 A | 6/1992 | Wiltrout et al. |
| 5,208,249 A | 5/1993 | Rowe et al. |
| 5,231,209 A | 7/1993 | Chung et al. |
| 5,290,578 A | 3/1994 | Passey et al. |
| 5,385,734 A | 1/1995 | Friedman |
| 5,411,986 A | 5/1995 | Cho et al. |
| 5,582,818 A | 12/1996 | Nakanishi et al. |
| 5,589,504 A | 12/1996 | Dannenberg et al. |
| 5,686,108 A | 11/1997 | Pusateri et al. |
| 5,725,895 A | 3/1998 | Fahey et al. |
| 5,882,646 A | 3/1999 | Pusateri et al. |
| 5,968,505 A | 10/1999 | Fahey et al. |
| 5,968,567 A | 10/1999 | Fahey et al. |
| 6,008,260 A | 12/1999 | Pezzuto et al. |
| 6,046,231 A | 4/2000 | Kosmeder, II et al. |
| RE36,784 E | 7/2000 | Cho et al. |
| 6,166,003 A | 12/2000 | Lam |
| 6,172,250 B1 | 1/2001 | Seguin et al. |
| 6,177,122 B1 | 1/2001 | Fahey et al. |
| 6,242,018 B1 | 6/2001 | Fahey et al. |
| 6,340,784 B1 | 1/2002 | Mithen et al. |

(Continued)

FOREIGN PATENT DOCUMENTS

| | | |
|---|---|---|
| CN | 101091705 | 12/2007 |
| EP | 0998943 | 5/2000 |

(Continued)

OTHER PUBLICATIONS

Zuang et al. Subgroup 2. Skin Irritation/Corrosion, in Cosmetics—European Commission, http://ec.europa.eu/consumers/sectors/cosmetics/files/doc/antest/(5)_chapter_3/2_skin_irritation_en.pdf., accessed Mar. 13, 2014.
Robert et al. New Engl. J. Med. 1999, 341 (24), 1817-1828.
Weber et al. The Journal of Emergency Medicine, 1999, 17 (2), 235-237.
Saint-Mezard et al. Eur. J. Dermatol. 2004, 14, 284-295.
PCT Written Opinion of the International Searching Authority for International Application No. PCT/US12/44660 dated Jul. 15, 2013.
PCT Written Opinion of the International Searching Authority for International Application No. PCT/US12/44593 dated Sep. 7, 2012.

(Continued)

*Primary Examiner* — Raymond J Henley, III
(74) *Attorney, Agent, or Firm* — King & Partners, PLC

(57) ABSTRACT

A formulation, including: (a) a first medicament, wherein the first medicament includes an isothiocyanate functional compound/surfactant; and (b) a second medicament, wherein the second medicament includes an antineoplastic agent, such as a cytotoxic antineoplastic agent and/or a targeted antineoplastic agent.

22 Claims, No Drawings

(56) References Cited

U.S. PATENT DOCUMENTS

| | | | |
|---|---|---|---|
| 6,348,220 B1 | 2/2002 | Ribnicky et al. |
| 6,414,037 B1 | 7/2002 | Pezzuto et al. |
| 6,436,450 B1 | 8/2002 | Omary et al. |
| 6,455,554 B1 | 9/2002 | Dull et al. |
| 6,465,512 B2 | 10/2002 | Nakamura et al. |
| 6,492,399 B1 | 12/2002 | Dull et al. |
| 6,524,594 B1 | 5/2003 | Santora et al. |
| 6,680,062 B2 | 1/2004 | Muizzuddin et al. |
| 6,737,441 B2 | 5/2004 | Fahey |
| 6,824,796 B2 | 11/2004 | Pusateri et al. |
| 6,878,751 B1 | 4/2005 | Donnelly et al. |
| 6,991,811 B1 | 1/2006 | Brovelli et al. |
| 7,303,770 B2 | 12/2007 | Fahey et al. |
| 7,402,569 B2 | 7/2008 | Fahey |
| 7,407,986 B2 | 8/2008 | Gao et al. |
| 7,615,657 B2 | 11/2009 | Bathurst et al. |
| 7,744,937 B2 | 6/2010 | West et al. |
| 7,820,145 B2 | 10/2010 | Tamarkin et al. |
| 7,879,822 B2 | 1/2011 | Dagan et al. |
| 8,003,633 B1 | 8/2011 | Robertson et al. |
| 8,008,281 B2 | 8/2011 | Prendergast et al. |
| 8,039,511 B2 | 10/2011 | Cheng et al. |
| 8,158,161 B2 | 4/2012 | Sussan et al. |
| 8,168,655 B2 | 5/2012 | Gadek et al. |
| 8,303,949 B2 | 11/2012 | Gao et al. |
| 8,309,541 B1 | 11/2012 | Robertson et al. |
| 8,410,037 B2 | 4/2013 | Molenda et al. |
| 8,410,170 B2 | 4/2013 | Cheng et al. |
| 8,492,616 B2 | 7/2013 | Mero |
| 8,510,127 B2 | 8/2013 | Hermann et al. |
| 8,709,406 B2 | 4/2014 | Gao et al. |
| 8,731,970 B2 | 5/2014 | Hermann et al. |
| 8,772,251 B2 | 7/2014 | Morazzoni et al. |
| 8,772,274 B1 | 7/2014 | Robertson et al. |
| 8,835,721 B2 | 9/2014 | Mero |
| 8,865,765 B2 | 10/2014 | Silver |
| 8,865,772 B2 * | 10/2014 | Silver | A61K 31/16 514/638 |
| 8,921,644 B2 | 12/2014 | Barten |
| 8,933,119 B2 | 1/2015 | Silver |
| 9,017,666 B2 | 4/2015 | Ashurst |
| 9,096,505 B2 | 8/2015 | Robertson et al. |
| 9,096,611 B2 | 8/2015 | Ren et al. |
| 9,126,910 B2 | 9/2015 | Robertson et al. |
| 9,126,911 B2 | 9/2015 | Robertson et al. |
| 9,131,722 B2 | 9/2015 | Kim et al. |
| 9,181,221 B2 | 11/2015 | Ren et al. |
| 9,254,331 B2 | 2/2016 | Dubois et al. |
| 9,308,192 B2 | 4/2016 | Coulombe et al. |
| 9,315,505 B2 | 4/2016 | Ren et al. |
| 9,359,349 B2 | 6/2016 | Ren et al. |
| 9,393,225 B2 | 7/2016 | Beumer et al. |
| 9,504,667 B2 * | 11/2016 | Silver | A61K 31/16 |
| 9,532,969 B2 | 1/2017 | Silver |
| 9,585,860 B2 | 3/2017 | Silver |
| 9,636,320 B2 * | 5/2017 | Silver | A61K 31/16 |
| 9,642,827 B2 * | 5/2017 | Silver | A61K 31/16 |
| 9,649,290 B2 | 5/2017 | Silver |
| 9,655,874 B2 | 5/2017 | Silver |
| 9,687,463 B2 | 6/2017 | Silver |
| 9,771,322 B2 | 9/2017 | Silver |
| 9,828,337 B2 | 11/2017 | Silver |
| 9,839,621 B2 * | 12/2017 | Silver | A61K 9/0014 |
| 9,931,314 B2 | 4/2018 | Silver |
| 9,932,306 B2 | 4/2018 | Silver |
| 9,949,943 B2 | 4/2018 | Silver |
| 9,951,003 B2 | 4/2018 | Silver |
| 9,951,004 B2 | 4/2018 | Silver |
| 9,951,005 B2 | 4/2018 | Silver |
| 9,962,361 B2 | 5/2018 | Silver |
| 10,010,520 B2 | 7/2018 | Cheng et al. |
| 10,080,734 B2 | 9/2018 | Silver |
| 10,111,851 B2 | 10/2018 | Silver |
| 10,111,852 B2 * | 10/2018 | Silver | A61K 9/0014 |
| 10,273,205 B2 | 4/2019 | Silver |
| 10,287,246 B2 | 5/2019 | Silver |
| 2002/0164381 A1 | 11/2002 | Shacknai et al. |
| 2003/0185864 A1 | 10/2003 | Kobayashi et al. |
| 2003/0198616 A1 | 10/2003 | Howard |
| 2004/0156873 A1 | 8/2004 | Gupta |
| 2005/0042182 A1 | 2/2005 | Arkin et al. |
| 2005/0095261 A1 | 5/2005 | Popp |
| 2005/0100621 A1 | 5/2005 | Popp et al. |
| 2005/0118124 A1 | 6/2005 | Reinhart et al. |
| 2005/0193448 A1 | 9/2005 | Gardner et al. |
| 2006/0127996 A1 | 6/2006 | Fahey |
| 2006/0160713 A1 | 7/2006 | Sekine et al. |
| 2007/0041925 A1 | 2/2007 | Picano et al. |
| 2008/0124407 A1 | 5/2008 | Eaton et al. |
| 2008/0154210 A1 | 6/2008 | Jordan et al. |
| 2008/0254150 A1 | 10/2008 | Rheins et al. |
| 2008/0306148 A1 | 12/2008 | Robertson et al. |
| 2008/0311192 A1 | 12/2008 | West et al. |
| 2008/0311276 A1 | 12/2008 | West et al. |
| 2009/0081138 A1 | 3/2009 | Ashurst |
| 2009/0186853 A1 | 7/2009 | Yu et al. |
| 2009/0324522 A1 | 12/2009 | Chevreau |
| 2010/0124598 A1 | 5/2010 | West et al. |
| 2011/0003747 A1 | 1/2011 | Coloumbe et al. |
| 2011/0014137 A1 | 1/2011 | Talalay et al. |
| 2011/0028548 A1 | 2/2011 | Fossel |
| 2011/0195103 A1 | 8/2011 | Perez Arcas et al. |
| 2012/0202878 A1 | 8/2012 | Silver |
| 2013/0079401 A1 | 3/2013 | Chen et al. |
| 2013/0116203 A1 | 5/2013 | Rajski et al. |
| 2014/0075590 A1 | 3/2014 | Van Den Bosch et al. |
| 2015/0038579 A1 | 2/2015 | Silver |
| 2015/0126600 A1 | 5/2015 | Silver |
| 2016/0015676 A1 | 1/2016 | Silver |
| 2016/0015677 A1 | 1/2016 | Silver |
| 2016/0022624 A1 | 1/2016 | Silver |
| 2016/0030379 A1 | 2/2016 | Silver |
| 2016/0030380 A1 | 2/2016 | Silver |
| 2016/0030381 A1 | 2/2016 | Silver |
| 2017/0037000 A1 | 2/2017 | Silver |
| 2017/0037001 A1 | 2/2017 | Silver |

FOREIGN PATENT DOCUMENTS

| | | |
|---|---|---|
| EP | 1 961 418 | 8/2008 |
| JP | 2000169321 | 6/2000 |
| JP | 2002284702 | 10/2002 |
| JP | 2008/193572 | 7/2006 |
| WO | WO 1994/005250 | 3/1994 |
| WO | WO 1994/019948 | 9/1994 |
| WO | WO 1997/007230 | 2/1997 |
| WO | WO 1997/026908 | 7/1997 |
| WO | WO 2005/016329 | 2/2005 |
| WO | WO 2006/065736 | 6/2006 |
| WO | WO 2007/056941 | 5/2007 |
| WO | WO 2008/070961 | 6/2008 |
| WO | WO 2009/014624 | 1/2009 |
| WO | WO 2009/088986 | 7/2009 |
| WO | WO 2010/140902 | 12/2010 |
| WO | WO 2012/010644 | 1/2012 |
| WO | WO 2012/064973 | 5/2012 |
| WO | WO 2013/003601 | 1/2013 |

OTHER PUBLICATIONS

PCT Written Opinion of the International Searching Authority for International Application No. PCT/US12/44628 dated Apr. 5, 2013.

PCT Written Opinion of the International Searching Authority for International Application No. PCT/US13/052307 dated Dec. 5, 2013.

Yehuda et al., Potential skin anti-inflammatory effects of 4-methylthiobutylisothiocyanate (MTBI) isolated from rocket (*Eruca sativa*) seeds, Biofactors 35(3), pp. 295-305, 2009. Abstract; p. 297, Fig. 1. https://www.researchgate.net/publication/24443311_Potential_skin_antiinflammatory_effects_of_4-methylthiobutylisothiocyanate_MTBI_isolated_from_rocket_Eruca_sativa_seeds.

Wikipedia—Isothiocyanate page, dated Aug. 22, 2014, pp. 1-4.

(56) References Cited

OTHER PUBLICATIONS

Romeo et al., Isothiocyanates: An Overview of Their Antimicrobial Activity Against Human Infections. Molecular Diversity Preservation International/Multidisciplinary Digital Publishing Institute (MDPI), Molecules 2016, 21, 626. pp. 1-28.
Dufour et al., The Antibacterial Properties of Isothiocyanates. Microbiology Research. Microbiology (2015), 161. pp. 229-243.
Valentine W. M. et al.: "Covalent Cross-Linking of Erythrocyte Spectrin by Carbon Disulfide in Vivo," Toxicology and Applied Pharmacology, Academic Press, Amsterdam, NL, vol. 121, No. 1, Jul. 1, 1993 pp. 71-77.
Sundaram G. S. M. et al.: "Synthesis of Bioorthogonal and Crosslinking Amino Acids for Use in Peptide Synthesis," Amino Acids; The Forum for Amino Acid and Protein Research, Springer-Verlag, VI, vol. 39, No. 5, Apr. 22, 2010, pp. 1381-1384.
Mironov et al.: "Synthesis and Properties of New Chlorin and Bacteriochlorin Photosensitizers," Proceedings of SPIE; Photochemistry; Photodynamic Therapy and Other Modalities. vol. 2625, Jan. 31, 1996, pp. 23-32.
Allyl Isothiocyante Product Safety Data Sheet. sc-252361, pp. 1-14.
Office Action for U.S. Appl. No. 13/342,516 dated May 22, 2013.
Office Action for U.S. Appl. No. 13/342,516 dated Mar. 18, 2014.
Office Action for U.S. Appl. No. 14/594,788 dated Sep. 30, 2015.
Office Action for U.S. Appl. No. 14/594,788 dated May 17, 2016.
Office Action for U.S. Appl. No. 14/880,408 dated Apr. 6, 2016.
Office Action for U.S. Appl. No. 14/880,408 dated Jul. 25, 2016.
Office Action for U.S. Appl. No. 14/880,408 dated Oct. 18, 2016.
Office Action for U.S. Appl. No. 14/880,418 dated Apr. 7, 2016.
Office Action for U.S. Appl. No. 14/880,418 dated Jul. 19, 2016.
Office Action for U.S. Appl. No. 14/880,418 dated Oct. 18, 2016.
Office Action for U.S. Appl. No. 14/880,426 dated Aug. 8, 2016.
Office Action for U.S. Appl. No. 14/880,426 dated Oct. 31, 2016.
Office Action for U.S. Appl. No. 13/348,821 dated Jan. 16, 2013.
Office Action for U.S. Appl. No. 13/348,821 dated Feb. 25, 2014.
Office Action for U.S. Appl. No. 14/519,462 dated Nov. 30, 2015.
Office Action for U.S. Appl. No. 14/519,462 dated Jul. 14, 2016.
Office Action for U.S. Appl. No. 14/868,897 dated Jun. 27, 2016.
Office Action for U.S. Appl. No. 14/868,929 dated Jul. 7, 2016.
Office Action for U.S. Appl. No. 14/868,959 dated Jul. 7, 2016.
Office Action for U.S. Appl. No. 13/952,236 dated Jun. 23, 2014.
Office Action for U.S. Appl. No. 14/519,510 dated Oct. 16, 2015.
Office Action for U.S. Appl. No. 14/519,510 dated Jun. 8, 2016.
Office Action for U.S. Appl. No. 14/867,585 dated Aug. 18, 2016.
Office Action for U.S. Appl. No. 14/867,626 dated Aug. 19, 2016.
Office Action for U.S. Appl. No. 13/351,616 dated Feb. 21, 2014.
Office Action for U.S. Appl. No. 13/351,616 dated Sep. 18, 2014.
Office Action for U.S. Appl. No. 13/351,616 dated Jan. 29, 2016.
Office Action for U.S. Appl. No. 14/594,788 dated Jul. 10, 2017.
Office Action for U.S. Appl. No. 14/594,788 dated Jun. 20, 2017.
Office Action for U.S. Appl. No. 14/594,788 dated Apr. 12, 2017.
Office Action for U.S. Appl. No. 14/880,418 dated Sep. 20, 2017.
Office Action for U.S. Appl. No. 15/296,701 dated Jun. 21, 2017.
Office Action for U.S. Appl. No. 15/296,701 dated May 3, 2017.
Office Action for U.S. Appl. No. 15/297,304 dated Jun. 20, 2017.
Office Action for U.S. Appl. No. 15/297,304 dated May 3, 2017.
Office Action for U.S. Appl. No. 15/634,639 dated Aug. 25, 2017.
Office Action for U.S. Appl. No. 15/397,375 dated Sep. 25, 2017.
Office Action for U.S. Appl. No. 15/590,645 dated Jun. 8, 2017.
Office Action for U.S. Appl. No. 15/353,260 dated Aug. 9, 2017.
Office Action for U.S. Appl. No. 15/459,822 dated Oct. 6, 2017.
Office Action for U.S. Appl. No. 15/675,915 dated Nov. 1, 2017.
Kricheldorf et al. Makromol. Chem. 1980, 181, 2571-2585.

* cited by examiner

ISOTHIOCYANATE FUNCTIONAL COMPOUNDS AUGMENTED WITH SECONDARY ANTINEOPLASTIC MEDICAMENTS AND ASSOCIATED METHODS FOR TREATING NEOPLASMS

CROSS-REFERENCE TO RELATED APPLICATIONS

This application is a continuation-in-part of U.S. application Ser. No. 16/025,640, entitled "METHOD FOR TREATING INFECTIOUS DISEASES WITH ISOTHIOCYANATE FUNCTIONAL COMPOUNDS" filed Jul. 2, 2018, which is a continuation-in-part of U.S. application Ser. No. 15/838,444, entitled "METHOD FOR TREATING BLADDER CANCER" filed Dec. 12, 2017, now U.S. Pat. No. 10,111,852, which is a continuation of U.S. application Ser. No. 15/423,869, entitled "METHOD FOR TREATING BLADDER CANCER" filed Feb. 3, 2017, now U.S. Pat. No. 9,839,621, which is a continuation-in-part of U.S. application Ser. No. 14/867,626, entitled "METHOD FOR TREATING SKIN CANCER," filed Sep. 28, 2015, now U.S. Pat. No. 9,642,827, which is a continuation of U.S. application Ser. No. 14/867,585, entitled "METHOD FOR TREATING SKIN CANCER," filed Sep. 28, 2015, now U.S. Pat. No. 9,636,320, which is a continuation of U.S. application Ser. No. 14/519,510, entitled "METHOD FOR TREATING SKIN CANCER," filed Oct. 21, 2014, now U.S. Pat. No. 9,504,667, which is a continuation of U.S. application Ser. No. 13/952,236, entitled "METHOD FOR TREATING SKIN CANCER," filed Jul. 26, 2013, now U.S. Pat. No. 8,865,772, which claims the benefit of U.S. Provisional Application Ser. No. 61/676,093, entitled "METHOD FOR TREATING SKIN CANCER," filed Jul. 26, 2012—which are hereby incorporated herein by reference in their entirety, including all references cited therein.

STATEMENT REGARDING FEDERALLY SPONSORED RESEARCH OR DEVELOPMENT

Not applicable.

REFERENCE TO A SEQUENCE LISTING

Not applicable.

BACKGROUND OF THE INVENTION

1. Field of the Invention

The present invention relates in general to medicament formulations and methods for treating neoplasms, and, more particularly, to methods for treating benign neoplasms, in situ neoplasms, malignant neoplasms, and/or neoplasms of uncertain or unknown behavior by administering an isothiocyanate functional compound augmented with a secondary, antineoplastic medicament to a patient having one or more neoplasms. The present invention also relates to the prophylactic administration of formulations disclosed herein.

2. Background Art

Neoplasms are ubiquitous—many forms of which have no known effective treatment and/or cure, and most of the current treatments for neoplasms, including, but not limited to, malignant neoplasms or cancers are replete with drawbacks, side effects, and/or toxicity issues.

It is therefore an object of the present invention to provide new, useful, and nonobvious medicament formulations and methods for treating and/or preventing benign neoplasms, in situ neoplasms, malignant neoplasms, and/or neoplasms of uncertain or unknown behavior.

These and other objects of the present invention will become apparent in light of the present specification, claims, and drawings.

SUMMARY OF THE INVENTION

The present invention is directed to a medicament formulation, comprising: (a) a first medicament, wherein the first medicament preferably comprises an isothiocyanate functional compound/surfactant; and (b) a second medicament, wherein the second medicament preferably comprises an antineoplastic agent, such as a cytotoxic antineoplastic agent and/or a targeted antineoplastic agent. The therapeutic effects on, for example, malignant neoplasms are believed to be enhanced by the synergistic effect of the two medicaments/active ingredients.

The present invention is also directed to a method for treating benign neoplasms, in situ neoplasms, malignant neoplasms, and/or neoplasms of uncertain or unknown behavior, comprising the step of: administering to a patient (e.g., mammal/human) a first medicament, wherein the first medicament preferably comprises an isothiocyanate functional compound/surfactant, and a second medicament, wherein the second medicament preferably comprises secondary, antineoplastic medicament—such as a cytotoxic antineoplastic agent and/or a targeted antineoplastic agent.

In a preferred embodiment of the present invention, the first and second medicaments are collectively and/or independently administered to the patient orally, intravenously, intramuscularly, intrathecally, cutaneously, subcutaneously, transdermally, sublingually, buccally, rectally, vaginally, ocularly, otically, and/or nasally. In this embodiment, the amount of isothiocyanate functional surfactant administered to the patient preferably ranges from approximately 0.5 nmol/cm2 to approximately 10 μmol/cm2 when topically administered.

In another preferred embodiment of the present invention, the weight ratio of the first medicament to the second medicament is approximately 1:1,000,000 to 1,000,000:1, 1:100,000 to 100,000:1, 1:10,000 to 10,000:1, 1:1,000 to 1,000:1, 1:500 to 500:1, 1:100 to 100:1, 1:10 to 10:1, and/or 1:1.

DETAILED DESCRIPTION OF THE INVENTION

While this invention is susceptible of embodiment in many different forms, there is shown in the drawings and/or described herein in detail several specific embodiments with the understanding that the present disclosure is to be considered as an exemplification of the principles of the invention and is not intended to limit the invention to the embodiments illustrated.

In accordance with the present invention, medicament formulations are disclosed herein, comprising: (a) a first medicament, wherein the first medicament preferably comprises an isothiocyanate functional compound/surfactant; and (b) a second medicament, wherein the second medicament preferably comprises an antineoplastic agent, such as a cytotoxic antineoplastic agent and/or a targeted antineoplastic agent. The medicament formulations of the present invention are used to treat and/or prevent, for example, benign neoplasms, in situ neoplasms, malignant neoplasms, and/or neoplasms of uncertain or unknown behavior. The therapeutic effects on, for example, malignant neoplasms or cancers are believed to be enhanced by the synergistic effect of the two medicaments/active ingredients. In particular, and especially for topical applications, the isothiocyanate functional compound/surfactant (i.e., the first medicament) permeates the skin and makes it easier for the second medicament or other actives (e.g., tertiary medicament, etcetera) to penetrate the skin. Once the isothiocyanate functional compound/surfactant has intercalated with the lipid bilayers of the stratum corneum, this leads to a looser, more permeable structure/environment. Unlike other presently available isothiocyanate compounds, the isothiocyanate functional compounds of the present invention are surfactants—and many are advantageously C12 surfactants and/or +/−C2. Therefore, it not only makes it easier for other antineoplastic agents and/or cancer drugs to penetrate into the skin, it also contributes its own antineoplastic activity as an isothiocyanate, hence the synergism.

In one embodiment, the present invention is directed to a method for treating and/or preventing benign neoplasms, in situ neoplasms, malignant neoplasms, and/or neoplasms of uncertain or unknown behavior, comprising the step of: administering to a patient (e.g., mammal/human) a first medicament, wherein the first medicament preferably comprises an isothiocyanate functional compound/surfactant, and a second medicament, wherein the second medicament preferably comprises secondary, antineoplastic medicament or other medicament. Preferably, the isothiocyanate functional surfactant comprises one or more isothiocyanate functional groups associated with an aliphatic and/or aromatic carbon atom of the isothiocyanate functional surfactant. It will be understood that isothiocyanate functional surfactants, regardless of their ordinary meaning, are defined herein as a surfactant having an isothiocyanate functional group associated therewith. It will be yet further understood that the term "associated" as used herein in chemical context, regardless of its ordinary meaning, is defined herein as attached, a covalent bond, a polar covalent bond, an ionic bond, a hydrogen bond, van der Waals forces, electrostatic interaction, directly and/or indirectly linked, etcetera.

The term surfactant derives from contraction of the terms surface-active-agent and is defined herein as a molecule and/or group of molecules which are able to modify the interfacial properties of the liquids (aqueous and non-aqueous) in which they are present. The surfactant properties of these molecules reside in their amphiphilic character which stems from the fact that each surfactant molecule has both a hydrophilic moiety and a hydrophobic (or lipophilic) moiety, and that the extent of each of these moieties is balanced so that at concentrations at or below the critical micelle concentration (i.e., CMC) they generally concentrate at the air-liquid interface and materially decrease the interfacial tension. For example, sodium salts of saturated carboxylic acids are extremely soluble in water up to C8 length and are thus not true surfactants. They become less soluble in water from C9 up to C18 length, the domain of effective surfactants for this class of compounds. The carboxylic acids (fatty acids) can be either saturated or unsaturated starting from C16 chain lengths.

Without being bound by any one particular theory, it is believed that the isothiocyanate functional surfactants disclosed herein facilitate treatment of neoplasms and/or neoplastic conditions by, elevating phase II enzymes (e.g., HAD(P)H quinine oxidoreductase) which are believed to, among other things regulate inflammatory responses within the body.

In accordance with the present invention, the isothiocyanate functional surfactants may be used as an administered leave-on/leave-in product in which one or more surfactants remain on/in the body and are not immediately and/or ever removed from the body. Alternatively, the isothiocyanate functional surfactants of the present invention may be used in an administer and remove fashion. For either case, it is preferred that the isothiocyanate functional surfactants be generally mild to human body (e.g., non-irritating or low-irritating). In particular, anionic N-alkanoyl surfactants derived from amino acids are especially preferred because, while not completely predictable, they have a tendency to be mild. The methods of preparation detailed in this invention employ, but are not limited to, amino acids that possess at least two amine functionalities, at least one of which is converted to an N-alkanoyl functionality, and at least one of which is converted into isothiocyanate functionality. The amino acids include, but are not limited to, the α-amino acids lysine, ornithine, 2,4-diaminobutanoic acid, 2,3-diaminopropionic acid, 2,7-diaminoheptanoic acid, and 2,8-diaminooctanoic acid. Additionally, amino acids other than α-amino acids may be employed, such as β-amino acids, etcetera. It will be understood that amino acid derived surfactants are preferred due to their mild nature, but any one of a number of other surfactants are likewise contemplated for use in accordance with the present invention.

Methods for preparing isothiocyanate functional surfactants and/or their precursors can involve, but are not limited to, conversion of an amine functionality to an isothiocyanate functionality. The methods of conversion of amine functionalities to isothiocyanate functionalities include, but are not limited to: (1) reaction with carbon disulfide to yield an intermediate dithiocarbamate, followed by reaction with ethylchloroformate or its functional equivalent such as bis (trichloromethyl)-carbonate, trichloromethyl chloroformate, or phosgene; (2) reaction with thiophosgene; (3) reaction with 1,1'-thiocarbonyldiimidizole; (4) reaction with phenyl-thiochloroformate; (5) reaction with ammonium or alkali metal thiocyanate to prepare an intermediate thiourea followed by cleaving to the isothiocyanate via heating; and (6) reaction with an isothiocyanato acyl halide [SCN—$(CH_2)_n$—CO—Cl]. The resulting isothiocyanate functional surfactant, depending on the method of preparation, can be isolated as a pure material or as a mixture with other surfactants. The resulting isothiocyanate functional surfactant, depending on the method of preparation, can be isolated and used directly in nonionic form, anionic form, cationic form, zwitterionic (amphoteric) form, and/or in a neutral surfactant-precursor form in combination with a base such as sodium hydroxide or triethanol amine if the neutral surfactant-precursor form possesses a protonated carboxylic acid group such that reaction (deprotonation) with the base converts the neutral surfactant-precursor form to an anionic surfactant, or in neutral surfactant-precursor form in combination with an acid if the neutral surfactant-precursor form possess amine functionality such that reaction (protonation) with the acid converts the neutral surfactant-precursor form to a cationic surfactant.

In accordance with the present invention the step of administering comprises, but is not limited to, systemic administration, local injection, regional injection, spraying, applying, dripping, dabbing, rubbing, blotting, dipping, and any combination thereof.

In one preferred embodiment of the present invention, the isothiocyanate functional surfactant is removed from body and/or affected area (e.g., in, on, and/or proximate to a neoplasm) after a period of time. Such a period comprises, but is not limited to, seconds (e.g., 1 second, 2 seconds, 5 seconds, 10 seconds, 15 seconds, 20 seconds, 30 seconds, 45 seconds, and 60 seconds), minutes (e.g., 1 minute, 2 minutes, 5 minutes, 10 minutes, 15 minutes, 20 minutes, 30 minutes, 45 minutes, and 60 minutes), hours (e.g., 1 hour, 2 hours, 4 hours, 5 hours, 8 hours, 10 hours, 15 hours, 24 hours, 36 hours, 48 hours, and 60 hours), days (e.g., 1 day, 2 days, 3 days, 4 days, 5 days, 6 days, 7 days, 10 days, 14 days, 21 days, 30 days), etcetera. It will be understood that the step of removing preferably occurs via purging, rinsing, wiping, and/or extracting—just to name a few.

Depending upon the subject and/or the severity of the condition and/or disease, multiple administrations may be necessary. As such, the steps of administering and/or removing the isothiocyanate functional surfactant may be repeated one or a plurality of times.

First Medicament

In a preferred embodiment of the present invention, the isothiocyanate functional surfactant comprises a lysine derivative, wherein the lysine derivative comprises an α-nitrogen and a ε-nitrogen, and wherein an alkyl and/or alkanoyl substituent comprising at least approximately 8 carbon atoms is associated with the α-nitrogen, and further wherein at least one isothiocyanate functional group is associated with the ε-nitrogen.

In one embodiment of the present invention, the isothiocyanate functional surfactant is represented by the following chemical structure:

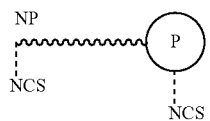

wherein the protonated form of the surfactant comprises a non-polar moiety (NP) and a polar moiety (P), and wherein at least one isothiocyanate functional group (NCS) is associated with the polar and/or non-polar moiety.

In accordance with a preferred embodiment of the present invention, the protonated form of the isothiocyanate functional surfactant is represented by the following chemical structure:

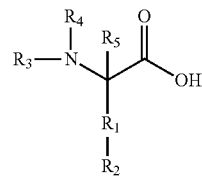

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; and wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s).

In a preferred embodiment of the present invention, the protonated form of the isothiocyanate functional surfactant is represented by the following chemical structure:

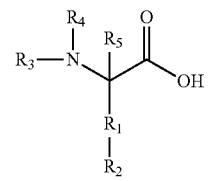

wherein $R_1$ is selected from the group consisting of an alkyl group containing 1 to 25 carbon atom(s); wherein $R_2$ is selected from the group consisting of NCS; and wherein $R_3$-$R_5$ are each independently selected from the group consisting of H; OH; and an alkyl, and alkanoyl group containing 1 to 25 carbon atom(s) with the proviso that at least one of $R_3$-$R_5$ is selected from the group consisting of an alkyl, and alkanoyl, group containing 8 to 25 carbon atoms.

In another preferred embodiment of the present invention, the protonated form of the isothiocyanate functional surfactant is represented by the following chemical structure:

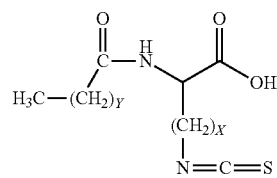

wherein X comprises an integer ranging from approximately 1 to approximately 25, and wherein Y comprises an integer ranging from approximately 6 to approximately 25. In this embodiment, the protonated form of the isothiocyanate functional surfactant is preferably represented by the following chemical structure:

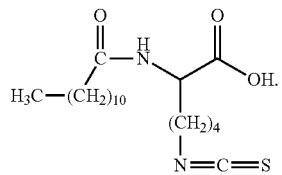

In yet another preferred embodiment of the present invention, the protonated form of the isothiocyanate functional surfactant is represented by at least one of the following chemical structures:
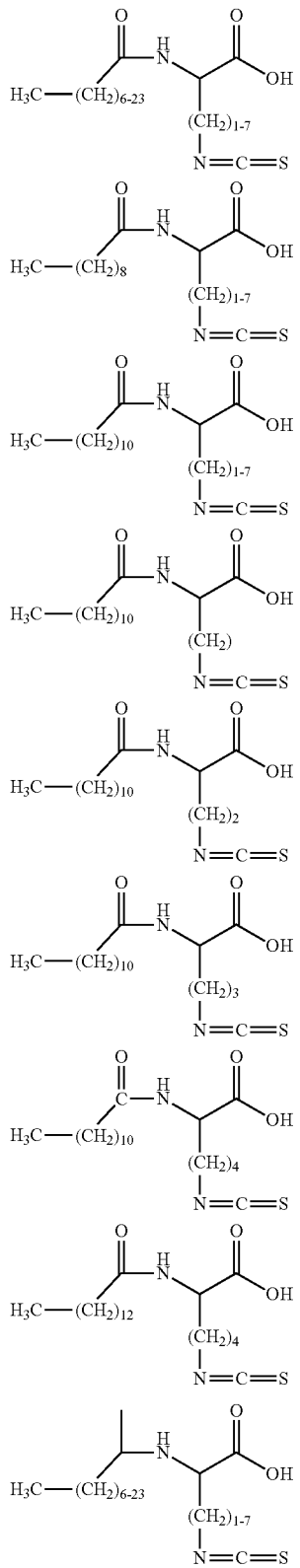
-continued
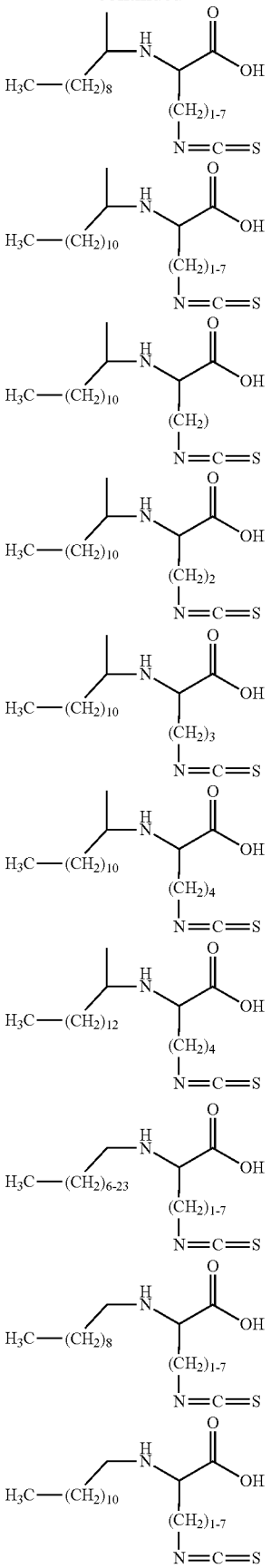

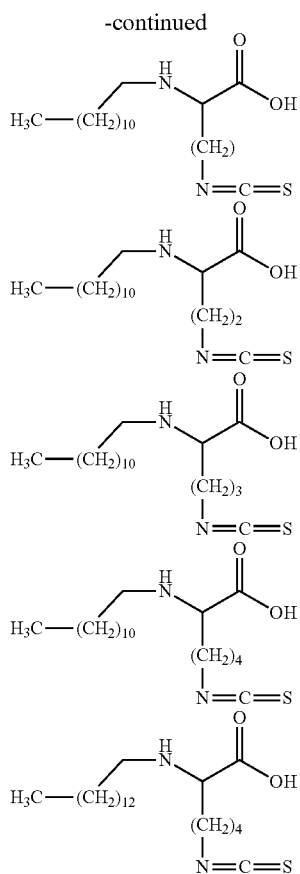

In another preferred embodiment of the present invention, the isothiocyanate functional surfactant is represented by the following chemical structure:

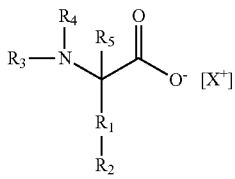

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s), wherein X comprises a counter cation such as, but not limited to, alkali metals, alkaline earth metals, transition metals, s-block metals, d-block metals, p-block metals, $NZ_4^+$, wherein Z comprises, H, $R_6$, $OR_6$, and wherein $R_6$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O and/or S containing moiety, and/or one or more functional groups comprising alcohols, esters, ammonium salts, phosphonium salts, and combinations thereof; a linkage to a dimer; a linkage to an oligomer; and/or a linkage to a polymer.

In yet another preferred embodiment of the present invention, the isothiocyanate functional surfactant is represented by the following chemical structure:

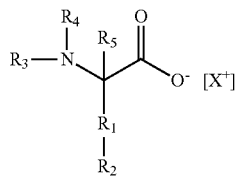

wherein $R_1$ is selected from the group consisting of an alkyl group containing 1 to 25 carbon atom(s); wherein $R_2$ is selected from the group consisting of NCS; and wherein $R_3$-$R_5$ are each independently selected from the group consisting of H; OH; and an alkyl, and alkanoyl group containing 1 to 25 carbon atom(s) with the proviso that at least one of $R_3$-$R_5$ is selected from the group consisting of an alkyl, and alkanoyl, group containing 8 to 25 carbon atoms; and wherein X comprises a counter cation.

In accordance with the present invention, the isothiocyanate functional surfactant may also be associated with one or more additional surfactants, wherein the additional surfactants are selected from at least one of the group comprising a non-ionic surfactant, an anionic surfactant, a cationic surfactant, a zwitterionic surfactant, and combinations thereof.

Non-limiting examples of preferred anionic surfactants include taurates; isethionates; alkyl and alkyl ether sulfates; succinamates; alkyl sulfonates, alkylaryl sulfonates; olefin sulfonates; alkoxy alkane sulfonates; sodium and potassium salts of fatty acids derived from natural plant or animal sources or synthetically prepared; sodium, potassium, ammonium, and alkylated ammonium salts of alkylated and acylated amino acids and peptides; alkylated sulfoacetates; alkylated sulfosuccinates; acylglyceride sulfonates, alkoxyether sulfonates; phosphoric acid esters; phospholipids; and combinations thereof. Specific anionic surfactants contemplated for use include, but are by no means limited to, ammonium cocoyl isethionate, sodium cocoyl isethionate, sodium lauroyl isethionate, sodium stearoyl isethionate, sodium lauroyl sarcosinate, sodium cocoyl sarcosinate, sodium lauryl sarcosinate, disodium laureth sulfosuccinate, sodium lauryl sulfoacetate, sodium cocoyl glutamate, TEA-cocoyl glutamate, TEA cocoyl alaninate, sodium cocoyl taurate, potassium cetyl phosphate.

Non-limiting examples of preferred cationic surfactants include alkylated quaternary ammonium salts $R_4NX$; alkylated amino-amides $(RCONH-(CH_2)_n)NR_3X$; alkylimidazolines; alkoxylated amines; and combinations thereof. Specific examples of anionic surfactants contemplated for use include, but are by no means limited to, cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, distearyl methyl ammonium chloride, distearyl methyl ammonium bromide, ditallow dimethyl ammonium chloride, ditallow dimethyl ammonium sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-imonium chloride phosphate, stearamidopropyl ethyldimonium ethosulfate, stearimidopropyldimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, ditallowyl oxyethyl dimethyl ammonium chloride, behenamidopropyl PG dimonium chloride, dilauryl dimethyl ammonium chloride, distearly dimethyl ammonium chloride, dimyristyl dimethyl ammonium chloride, dipalmityl dimethyl ammonium chloride, distearyl dimethyl ammonium chloride, stearamidoproyl PG-dimonium chloride phosphate, stearamidopropyl ethyldiammonium ethosulfate, stearamidopropyl dimethyl (myristyl acetate) ammonium chloride, stearimidopropyl dimethyl cetaryl ammonium tosylate, stearamido propyl dimethyl ammonium chloride, stearamidopropyl dimethyl ammonium lactate.

Non-limiting examples of preferred non-ionic surfactants include alcohols, alkanolamides, amine oxides, esters (including glycerides, ethoxylated glycerides, polyglyceryl esters, sorbitan esters, carbohydrate esters, ethoxylated carboxylic acids, phosphoric acid triesters), ethers (including ethoxylated alcohols, alkyl glucosides, ethoxylated polypropylene oxide ethers, alkylated polyethylene oxides, alkylated polypropylene oxides, alkylated PEG/PPO copolymers), silicone copolyols. Specific examples of non-ionic surfactants contemplated for use include, but are by no means limited to, cetearyl alcohol, ceteareth-20, nonoxynol-9, C12-15 pareth-9, POE(4) lauryl ether, cocamide DEA, glycol distearate, glyceryl stearate, PEG-100 stearate, sorbitan stearate, PEG-8 laurate, polyglyceryl-10 trilaurate, lauryl glucoside, octylphenoxy-polyethoxyethanol, PEG-4 laurate, polyglyceryl diisostearate, polysorbate-60, PEG-200 isostearyl palm itate, sorbitan monooleate, polysorbate-80.

Non-limiting examples of preferred zwitterionic or amphoteric surfactants include betaines; sultaines; hydroxysultaines, amido betaines, amidosulfo betaines; and combinations thereof. Specific examples of amphoteric surfactants contemplated for use include, but are by no means limited to, cocoamidopropyl sultaine, cocoamidopropyl hydroxyl sultaine, cocoamidopropylbetaine, coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl (2-bishydroxy) carboxymethyl betaine, stearyl bis-(2-hydroxyethyl) carboxymethyl betaine, oelyl dimethyl gamma-carboxypropyl betaine, lauryl bis-(2-hydroxypropyl)alpha carboxymethyl betaine, coco dimethyl sulfopropyl betaine, stearyl dimethyl sulfopropyl betaine, lauryl dimethyl sulfoethyl betaine, lauryl bis(2-hydroxyethyl) sulfopropyl betaine, oleyl betaine, cocamidopropyl betaine.

Second Medicament

In a preferred embodiment of the present invention, the second medicament comprises a cytotoxic antineoplastic agent selected from the group comprising nucleoside analogues (e.g., azacytidine, capecitabine, carmofur, cladribine, clofarabine, cytarabine, decitabine, floxuridine, fludarabine, fluorouracil, gemcitabine, mercaptopurine, nelarabine, pentostatin, tegafur, tioguanine, etcetera), antifolates (e.g., methotrexate, pemetrexed, raltitrexed, etcetera), antimetabolites (e.g., hydroxycarbamide, etcetera), topoisomerase inhibitors (e.g., irinotecan, topotecan, etcetera), anthracyclines (e.g., daunorubicin, doxorubicin, epirubicin, idarubicin, mitoxantrone, valrubicin, etcetera), podophyllotoxins (e.g., etoposide, teniposide, etcetera), taxanes (e.g., cabazitaxel, docetaxel, paclitaxel, etcetera), vinca alkaloids (e.g., vinblastine, vincristine, vindesine, vinflunine, vinorelbine, etcetera), alkylating agents (e.g., bendamustine, busulfan, carmustine, chlorambucil, chlormethine, cyclophosphamide, dacarbazine, fotemustine, ifosfamide, lomustine, melphalan, streptozotocin, temozolomide, etcetera), metal/platinum compounds (e.g., carboplatin, cisplatin, nedaplatin, oxaliplatin, etcetera), and/or other non-categorized cytotoxic antineoplastic agents (e.g., altretamine, bleomycin, bortezomib, dactinomycin, estramustine, ixabepilone, mitomycin, procarbazine, etcetera).

In another preferred embodiment of the present invention, the cytotoxic antineoplastic agents are represented by one or more of the following chemical structures:

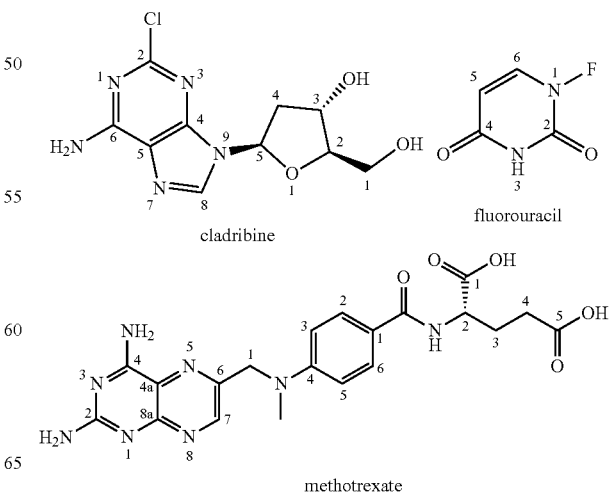

cladribine fluorouracil methotrexate

-continued

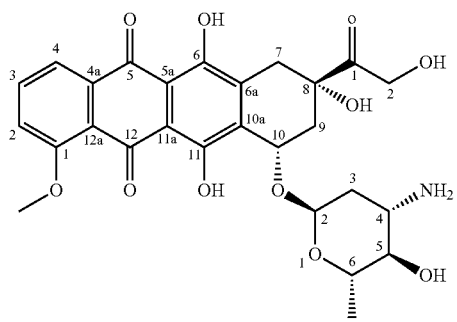
doxorubicin

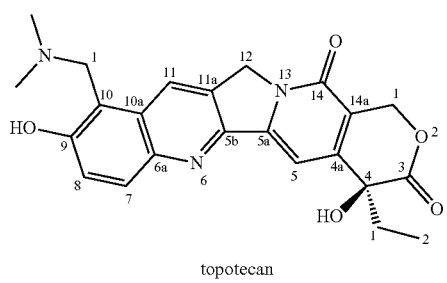
topotecan

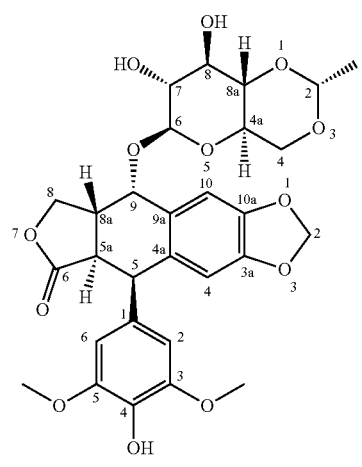
etoposide

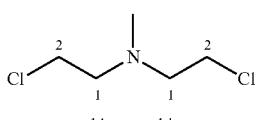
chloromethine

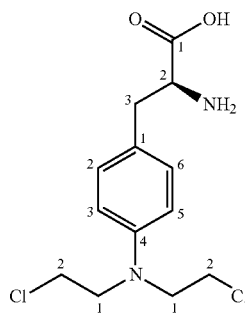
melphalan

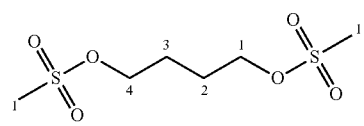
busulfan

-continued

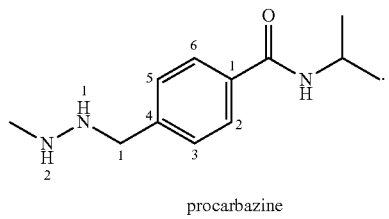
procarbazine

In a preferred embodiment of the present invention, the second medicament comprises a targeted antineoplastic agent selected from the group comprising monoclonal antibodies (e.g., alemtuzumab, bevacizumab, cetuximab, denosumab, gemtuzumab ozogamicin, ibritumomab tiuxetan, ipilimumab, nivolumab, ofatumumab, panitumumab, pembrolizumab, pertuzumab, rituximab, tositumomab, trastuzumab, etcetera), tyrosine kinase inhibitors (e.g., afatinib, aflibercept, axitinib, bosutinib, crizotinib, dasatinib, erlotinib, gefitinib, imatinib, lapatinib, nilotinib, pazopanib, ponatinib, regorafenib, ruxolitinib, sorafenib, sunitinib, vandetanib, etcetera), mTOR inhibitors (e.g., everolimus, temsirolimus, etcetera), retinoids (e.g., alitretinoin, bexarotene, isotretinoin, tamibarotene, tretinoin, etcetera), immunomodulatory agents (e.g., lenalidomide, pomalidomide, thalidomide, etcetera), histone deacetylase inhibitors (e.g., romidepsin, valproate, vorinostat, etcetera), and/or other non-categorized targeted antineoplastic agents (e.g., anagrelide, arsenic trioxide, asparaginase, bcg vaccine, denileukin diftitox, vemurafenib, etcetera).

In another preferred embodiment of the present invention, the targeted antineoplastic agents are represented by one or more of the following chemical structures:

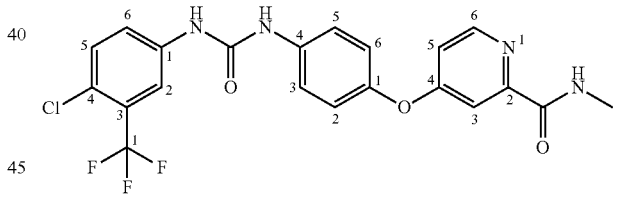
sorafenib

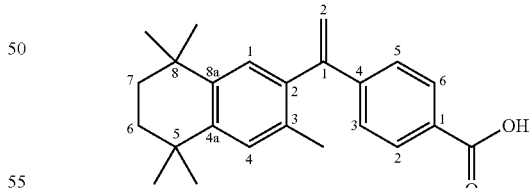
bexarotene

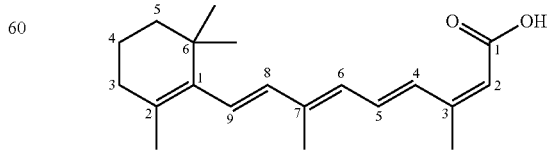
isotretinoin

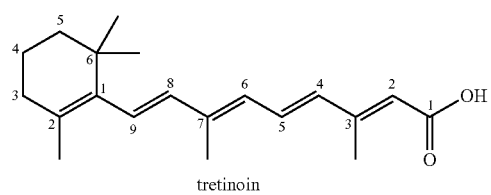
tretinoin

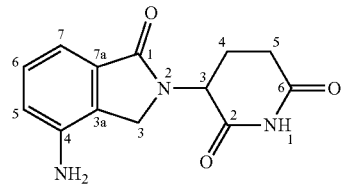
lenalidomide

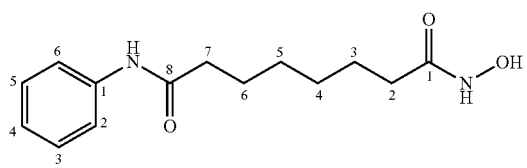
vorinostat

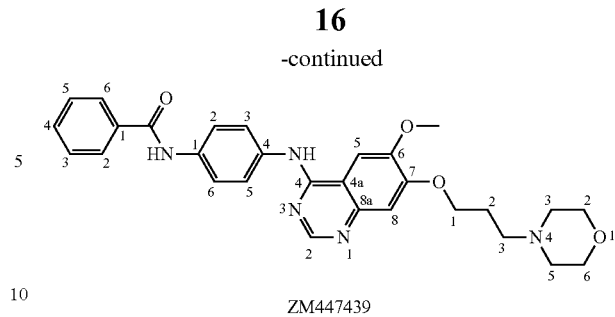
ZM447439

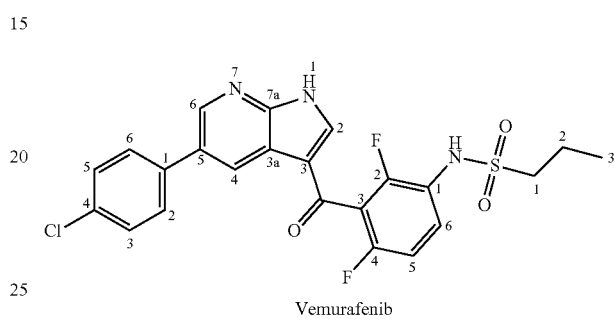
Vemurafenib

In one embodiment of the present invention, the second medicament comprises at least one of a DNA-effecting or influencing anti-cancer medicament, a kinase-inhibiting anti-cancer medicament, an anti-androgen medicament (e.g., bicalutamide, flutamide, nilutamide, etcetera), and/or a hormonal anti-cancer medicament. In this embodiment, the second medicaments are preferably represented by one or more of the following chemical structures:

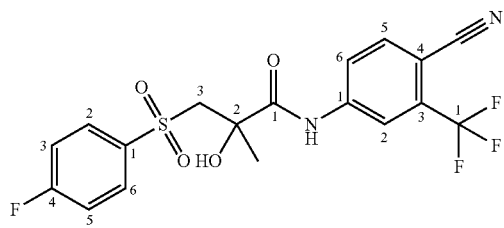
bicalutamide

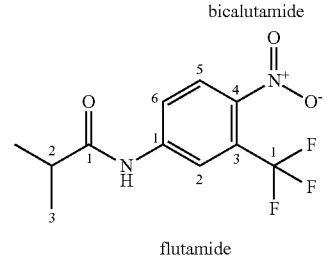
flutamide

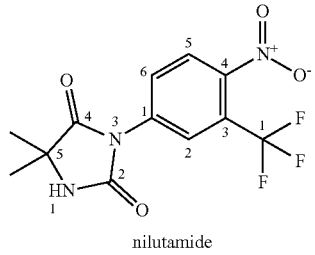
nilutamide

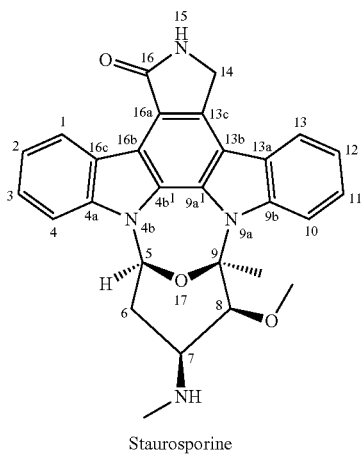
Staurosporine

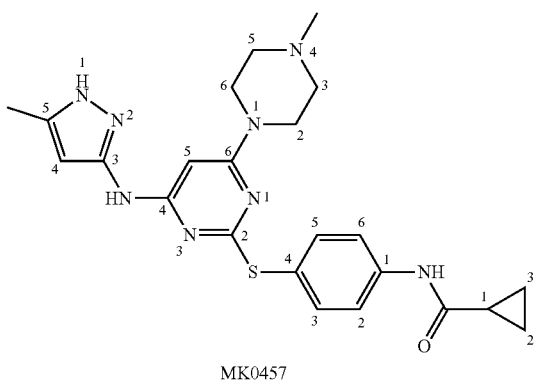
MK0457

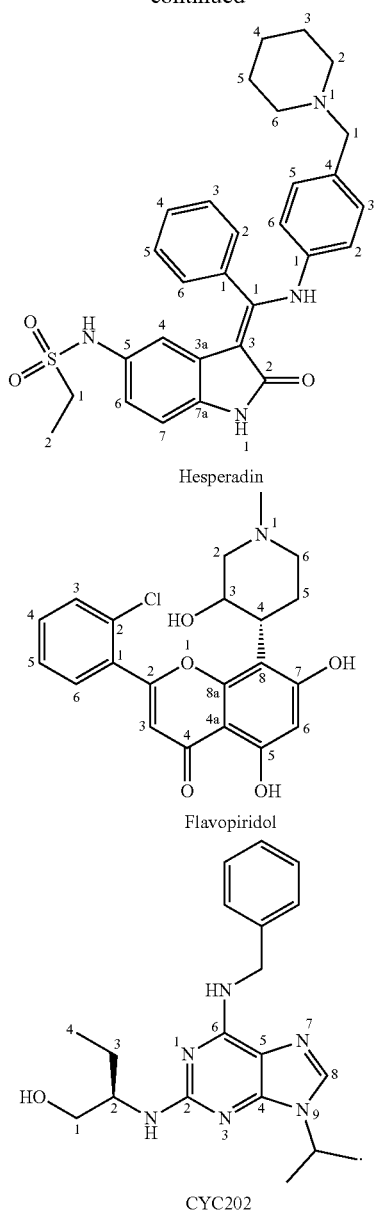

Hesperadin

Flavopiridol

CYC202

Additional, non-limiting examples of secondary and/or tertiary medicaments include those disclosed in U.S. Pat. No. 10,010,520, entitled "COMBINED APPLICATION OF ISOTHIOCYANATE COMPOUND AND ANTI-CANCER MEDICINE," which is hereby incorporated herein by reference in its entirety, including all references cited therein.

In further accordance with the present invention, the first and second medicaments may optionally be incorporated into a formulation comprising one or more polar and/or non-polar solvents. Preferably, the solvent comprises a hydrocarbon and/or silicone oil that is generally non-hygroscopic and/or generally hydrophobic. Suitable examples, include, silicone-based solvents and/or fluids, mineral oil, vegetable oils, squalene (i.e., 2,6,10,15,19,23-hexamethyltetracosane)—just to name a few.

Additional agents that are used in oncology are likewise contemplated for use in the formulations and treatment methods of the present invention, including, but not limited to, antiemetics, hematopoietic growth factors (e.g., erythropoietin, GCSF, oprelvekin, pegfilgrastim, GMCSF, etcetera), other marrow stimulating agents (e.g., eltrombopag, plerixafor, romiplostim, etcetera), immunosuppressants (e.g., basiliximab, cyclosporine, mycophenolic acid, etctera), anti-complement therapy (e.g., eculizumab, etctera), bone resorption modifiers (e.g., calcitonin, cinacalcet, denosumab, pamidronate, zoledronate, etctera), toxicity modifiers (e.g., allopurinol, amifostine, dexrazoxane, glucarpidase, methylene blue, mesna, palifermin, rasburicase, etctera), medications for infections, anticoagulants and thrombolytic agents such as alteplase for central venous access device clearance, replacement therapies (e.g., folate, intravenous iron, vitamin $B_{12}$, etctera), iron binding agents (e.g., deferasirox, deferiprone, deferoxamine, etctera) and/or diagnostic agents (e.g., fluciclovine).

In a preferred embodiment of the present invention, the first and second medicaments are collectively and/or independently administered to the patient orally, intravenously, intramuscularly, intrathecally, cutaneously, subcutaneously, transdermally, sublingually, buccally, rectally, vaginally, ocularly, otically, and/or nasally. In this embodiment, the amount of isothiocyanate functional surfactant administered to the patient preferably ranges from approximately 0.5 nmol/cm2 to approximately 10 μmol/cm2 when topically administered.

In another preferred embodiment of the present invention, the weight ratio of the first medicament to the second medicament is approximately 1:1,000,000 to 1,000,000:1, 1:100,000 to 100,000:1, 1:10,000 to 10,000:1, 1:1,000 to 1,000:1, 1:500 to 500:1, 1:100 to 100:1, 1:10 to 10:1, and/or 1:1.

The invention is further described by the following examples.

EXAMPLE I

Preparation of a Mixture of $N_\alpha$-lauroyl-$N_\epsilon$-isothiocyanato-L-Lysine with $N_\alpha$, $N_\epsilon$-bis-lauroyl-L-lysine A 1 liter beaker equipped with an overhead mechanical stainless steel paddle stirrer was charged with 100 mL of 1 M NaOH (0.100 mol). Stirring was begun and the beaker cooled to −5° C. to −10° C. using a salt/ice bath. Next, 23.4 g (0.100 mol) of $N_\epsilon$-benzylidene-L-lysine (prepared via the method of Bezas, B and Zervas, L., JACS, 83, 1961, 719-722) was added. Immediately afterward and while keeping the solution cold, 140 mL (0.140 mol) of precooled (in a salt/ice bath) 1 M NaOH and 26.1 mL of lauroyl chloride was added in two equal portions over a period of 6 minutes. The mixture was stirred for 10 more minutes at −5 to −10° C., then the ice bath was removed and the reaction mixture allowed to stir for another 1 hour while warming to room temperature. Next, the reaction mixture was cooled using a salt/ice bath and then sufficient concentrated HCl was added to adjust the pH to 7.5-7.8. With the pH at 7.8-7.8 and with continued cooling and stirring, 4.6 mL (60% of stoichiometric, 0.068 mol) of thiophosgene was added dropwise via an additional funnel over the period of 1 hour. During this time, sufficient 1 M NaOH was added to maintain a pH range between 7.5-7.8. After the thiophosgene addition was complete, additional 1 M NaOH was added as necessary until the pH stabilized in 7.5-7.8 range. Next, sufficient 30% NaOH was added to adjust the pH to approximately 8.5. Next, 12 mL (0.051 mol) of lauroyl chloride was rapidly added, followed by sufficient 1 M NaOH to keep the pH in the range of 8.00-8.50. Next, sufficient concentrated HCl was added to adjust the pH to 1.5. The reaction mixture was filtered via vacuum filtration, and the precipitate washed with dilute HCl (pH=2). The product, a white moist solid, was dried in vacuo while heating to 60° C. 45.19 g of white solid product was recovered, a mixture of predominantly $N_\alpha$-lauroyl-$N_\epsilon$-isothiocyanato-L-lysine and $N_\alpha$, $N_\epsilon$-bis-lauroyl-L-lysine (determined via LC-MS analysis). Both compounds in this mixture can be simultaneously converted into anionic (carboxylate) surfactants via reaction with aqueous NaOH to yield a clear aqueous solution of the surfactants.

EXAMPLE II

Preparation of Pure $N_\alpha$-lauroyl-$N_\epsilon$-isothiocyanato-L-Lysine

Step 1: Preparation of $N_\alpha$-lauroyl-$N_\epsilon$-carbobenzoxy-L-Lysine 60.0 g of $N_\epsilon$-cbz-L-Lysine (cbz is carbobenzoxy) purchased from Atomole Scientific Company, LTD was added to a three-liter beaker along with 1200 mL of RO water and the mixture was stirred. Next, 39 mL of 30% aqueous NaOH was added, resulting in dissolution of the $N_\epsilon$-cbz-L-Lysine. The resulting solution was cooled in an ice bath and then 52.5 mL of lauroyl chloride was added. The ice bath was removed 30 minutes later, and stirring continued for an additional six hours, at which time 18 mL of concentrated hydrochloric acid was added. The reaction mixture was then filtered via vacuum filtration, the white solid product washed with 1 M aqueous HCl, and then the solid product was dried in vacuo while heated to approximately 85° C. 96.5 g of dry white solid product was obtained. The product can be further purified by dissolving it in methanol, filtering off any insoluble precipitate, and removing the methanol in vacuo to recover a white solid product (mp 99.5-103.0° C.)

Step 2: Preparation of $N_\alpha$-lauroyl-NE-ammonium chloride-L-Lysine 10.0 g of $N_\alpha$-lauroyl-$N_\epsilon$-carbobenzoxy-L-Lysine was weighed into a one liter Erlenmeyer flask equipped with a magnetic stir bar. 150 mL of concentrated hydrochloric acid was added and the solution was stirred and heated in an oil bath to 104° C., then allowed to cool with the oil bath back to room temperature. The solution was then cooled to 9° C. for approximately four hours, during which time a large mass of white precipitate formed. The reaction mixture was filtered in vacuo and rinsed with a small amount of cold 1 M HCl. The white solid reaction product was then dried in vacuo while being heated to 78° C., yielding 7.89 g of white solid product (mp 191-193° C.).

Step 3: Preparation of $N_\alpha$-lauroyl-$N_\epsilon$-isothiocyanato-L-Lysine 0.46 mL of thiophosgene was added to 30 mL of dichloromethane in a 125 mL Erlenmeyer flask equipped with a magnetic stir bar. To this solution was drop wise added over 15 minutes a solution consisting of 2.00 g $N_\alpha$-lauroyl-$N_\epsilon$-ammonium chloride-L-Lysine, 10 mL RO water, and 2.7 mL 20% aqueous NaOH. Stirring was continued for an additional 30 minutes, after which sufficient concentrated hydrochloric acid was added to lower the pH to 1 as indicated by testing with pHydrion paper. The reaction solution was then transferred into a separatory funnel and the bottom turbid dichloromethane layer was isolated and dried with anhydrous magnesium sulfate and gravity filtered. To the filtrate was added 50 mL of hexanes. The solution was then concentrated via removal of 34 mL of solvent via trap-to-trap distillation and then placed in a −19° C. freezer. A mass of white precipitate formed after a few hours and was isolated via vacuum filtration and then dried in vacuo for 2 hours. 1.130 g of a slightly off white solid powder product was obtained [mp 37.0-39.0° C.; IR (cm$^{-1}$), 3301sb, 2923s, 2852s, 2184m, 2099s, 1721s, 1650s, 1531s, 1456m, 1416w, 1347m, 1216m, 1136w].

The oils and/or solvents employed hereinabove are provided for the purposes of illustration, and are not to be construed as limiting the invention in any way. As such, the oils may be liquid, solid, or gel, and may be synthetic or of natural origin and include but are not limited to waxes, esters, lipids, fats, glycerides, cyclic silicones, linear silicones, crosslinked silicones, alkylsilicones, silicone copolyols, alkylated silicone copolyols, and/or hydrocarbons, and/or ethoxylated versions of all of these.

The foregoing description merely explains and illustrates the invention and the invention is not limited thereto except insofar as the appended claims are so limited, as those skilled in the art who have the disclosure before them will be able to make modifications without departing from the scope of the invention.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etcetera shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etcetera. As a non-limiting example, each range discussed herein can be readily broken down into a lower third, middle third and upper third, etcetera. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed and desired to be secured by Letters Patent of the United States is:

1. A medicament formulation, comprising:
   a first medicament, wherein the first medicament comprises an isothiocyanate functional surfactant; and
   a second medicament, wherein the second medicament comprises an antineoplastic agent.

2. The medicament formulation according to claim 1, wherein the isothiocyanate functional surfactant comprises at least one isothiocyanate functional group associated with an aliphatic and/or aromatic carbon atom of the isothiocyanate functional surfactant.

3. The medicament formulation according to claim 1, wherein the isothiocyanate functional surfactant comprises a lysine derivative, wherein the lysine derivative comprises an α-nitrogen and a ε-nitrogen, and wherein an alkyl and/or alkanoyl substituent comprising at least approximately 8 carbon atoms is associated with the α-nitrogen, and further wherein at least one isothiocyanate functional group is associated with the ε-nitrogen.

4. The medicament formulation according to claim 1, wherein the isothiocyanate functional surfactant is represented by the following chemical structure:

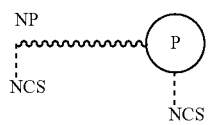

wherein the protonated form of the surfactant comprises a non-polar moiety (NP) and a polar moiety (P), and wherein at least one isothiocyanate functional group (NCS) is associated with the polar and/or non-polar moiety.

5. The medicament formulation according to claim 1, wherein the protonated form of the isothiocyanate functional surfactant is represented by the following chemical structure:

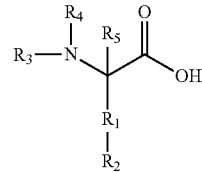

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; and wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s).

6. The medicament formulation according to claim 1, wherein the protonated form of the isothiocyanate functional surfactant is represented by the following chemical structure:

wherein $R_1$ is selected from the group consisting of an alkyl group containing 1 to 25 carbon atom(s); wherein $R_2$ is selected from the group consisting of NCS; and wherein $R_3$-$R_5$ are each independently selected from the group consisting of H; OH; and an alkyl, and alkanoyl group containing 1 to 25 carbon atom(s) with the proviso that at least one of $R_3$-$R_5$ is selected from the group consisting of an alkyl, and alkanoyl, group containing 8 to 25 carbon atoms.

7. The medicament formulation according to claim 1, wherein the protonated form of the isothiocyanate functional surfactant is represented by the following chemical structure:

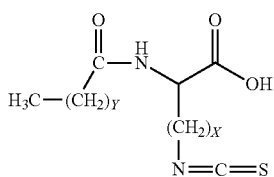

wherein X comprises an integer ranging from approximately 1 to approximately 25, and wherein Y comprises an integer ranging from approximately 6 to approximately 25.

8. The medicament formulation according to claim 1, wherein the protonated form of the isothiocyanate functional surfactant is represented by the following chemical structure:

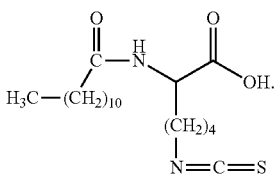

9. The medicament formulation according to claim 1, wherein the protonated form of the isothiocyanate functional surfactant is represented by at least one of the following chemical structures:

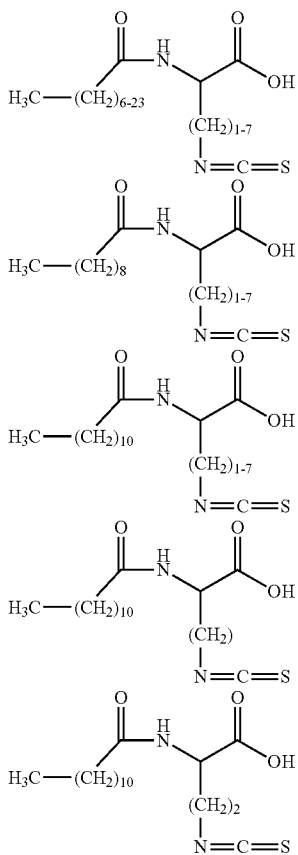

-continued

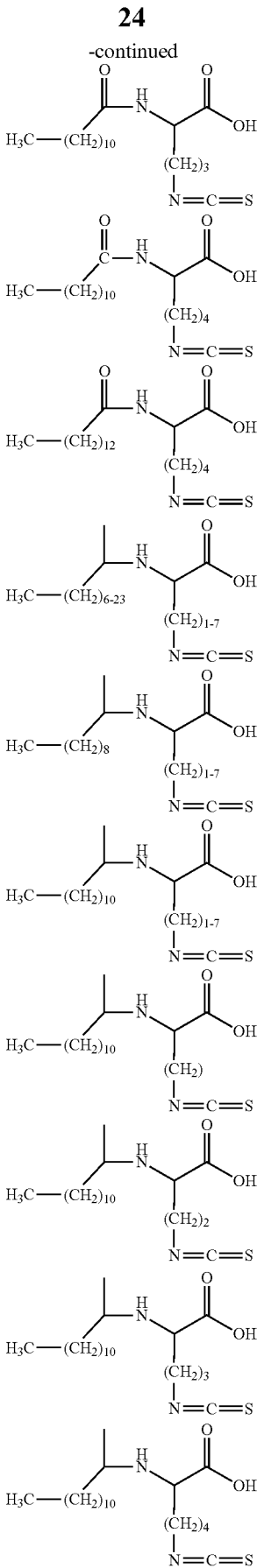

-continued

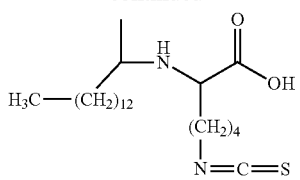

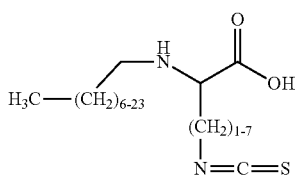

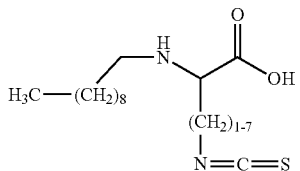

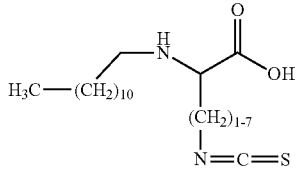

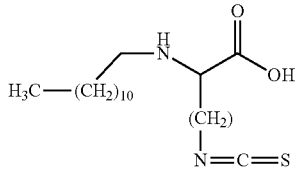

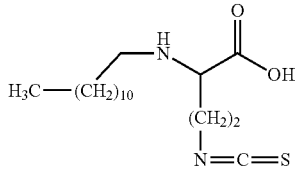

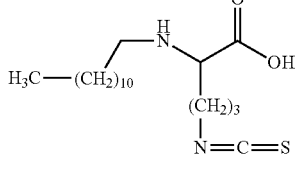

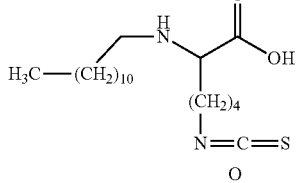

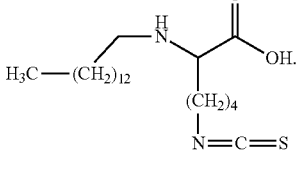

10. The medicament formulation according to claim 1, wherein the isothiocyanate functional surfactant is represented by the following chemical structure:

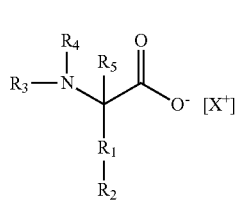

wherein $R_1$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer; wherein $R_2$ comprises NCS; wherein $R_3$-$R_5$ are the same or different and comprise H; OH; an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer with the proviso that at least one of $R_3$-$R_5$ comprise an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 8 to approximately 25 carbon atom(s), wherein X comprises a counter cation such as, but not limited to, alkali metals, alkaline earth metals, transition metals, s-block metals, d-block metals, p-block metals, $NZ_4^+$, wherein Z comprises, H, $R_6$, $OR_6$, and wherein $R_6$ comprises an alkyl, cycloalkyl, polycycloalkyl, heterocycloalkyl, aryl, alkaryl, aralkyl, alkoxy, alkanoyl, aroyl, alkenyl, alkynyl and/or cyano group containing approximately 1 to approximately 25 carbon atom(s), wherein the carbon atom(s) may be a linking group to, or part of, a halogen, a N, O, and/or S containing moiety, and/or one or more functional groups comprising alcohols, esters, ammonium salts, phosphonium salts, and combinations thereof; a linkage to a dimer; a linkage to an oligomer; and/or a linkage to a polymer.

11. The medicament formulation according to claim 1, wherein the isothiocyanate functional surfactant is represented by the following chemical structure:

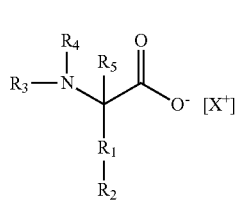

wherein $R_1$ is selected from the group consisting of an alkyl group containing 1 to 25 carbon atom(s); wherein $R_2$ is selected from the group consisting of NCS; and wherein $R_3$-$R_5$ are each independently selected from the group consisting of H; OH; and an alkyl, and alkanoyl group containing 1 to 25 carbon atom(s) with the proviso that at least one of $R_3$-$R_5$ is selected from the group consisting of an alkyl, and alkanoyl, group containing 8 to 25 carbon atoms; and wherein X comprises a counter cation.

12. The medicament formulation according to claim 1, wherein the second medicament comprises at least one of a cytotoxic antineoplastic agent and a targeted antineoplastic agent.

13. The medicament formulation according to claim 1, wherein the second medicament comprises a cytotoxic antineoplastic agent selected from the group comprising a nucleoside analogue, an antifolate, an antimetabolite, a topoisomerase inhibitor, a anthracycline, a podophyllotoxin, a taxane, a vinca alkaloid, an alkylating agent, and/or a platinum compound.

14. The medicament formulation according to claim 1, wherein the second medicament comprises a monoclonal antibody, a tyrosine kinase inhibitor, an mTOR inhibitor, a retinoid, an immunomodulatory agent, and/or a histone deacetylase inhibitor.

15. The medicament formulation according to claim 1, wherein the second medicament comprises a DNA-effecting or influencing anti-cancer medicament, a kinase-inhibiting anti-cancer medicament, an anti-androgen medicament and/or a hormonal anti-cancer medicament.

16. The medicament formulation according to claim 1, wherein the second medicament comprises bicalutamide.

17. The medicament formulation according to claim 1, wherein the second medicament comprises fluorouracil.

18. The medicament formulation according to claim 1, wherein the second medicament comprises chlormethine.

19. The medicament formulation according to claim 1, wherein the second medicament comprises at least one of bevacizumab, cetuximab, denosumab, gemtuzumab ozogamicin, ibritumomab tiuxetan, ipilimumab, nivolumab, ofatumumab, panitumumab, pembrolizumab, pertuzumab, rituximab, tositumomab, and trastuzumab.

20. The medicament formulation according to claim 1, wherein the second medicament comprises at least one of alitretinoin, bexarotene, isotretinoin, tamibarotene, and tretinoin.

21. A medicament formulation, comprising:
a first medicament, wherein the first medicament comprises an isothiocyanate functional surfactant represented by the following chemical structure:

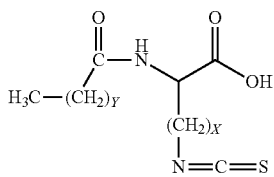

wherein X comprises an integer ranging from 1 to 25, and wherein Y comprises an integer ranging from 6 to 25; and a second medicament, wherein the second medicament comprises at least one of bicalutamide, fluorouacil, chlormethine, bevacizumab, cetuximab, denosumab, gemtuzumab ozogamicin, ibritumomab tiuxetan, ipilimumab, nivolumab, ofatumumab, panitumumab, pembrolizumab, pertuzumab, rituximab, tositumomab, trastuzumab, alitretinoin, bexarotene, isotretinoin, tamibarotene, and tretinoin.

22. A medicament formulation, comprising:
a first medicament, wherein the first medicament comprises an isothiocyanate functional surfactant represented by at least one of the following chemical structures:

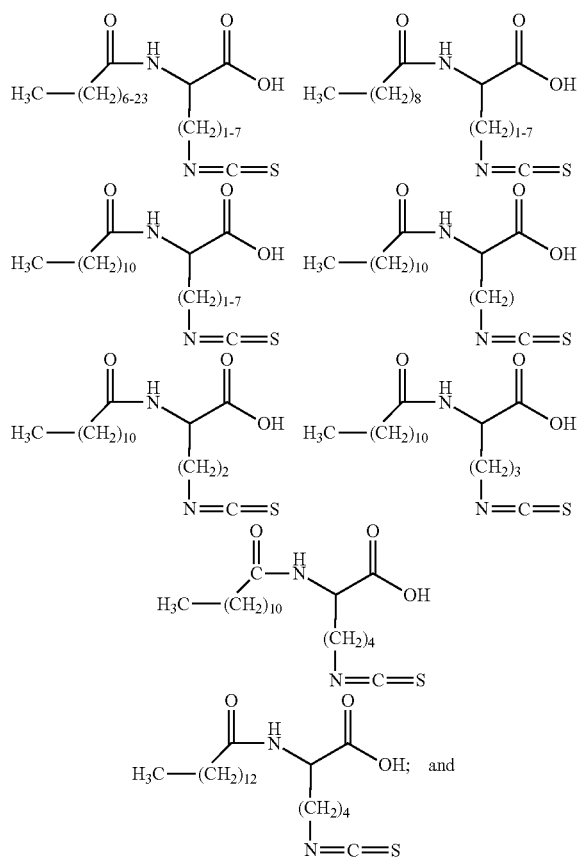

a second medicament, wherein the second medicament comprises at least one of bicalutamide, fluorouacil, chlormethine, bevacizumab, cetuximab, denosumab, gemtuzumab ozogamicin, ibritumomab tiuxetan, ipilimumab, nivolumab, ofatumumab, panitumumab, pembrolizumab, pertuzumab, rituximab, tositumomab, trastuzumab, alitretinoin, bexarotene, isotretinoin, tamibarotene, and tretinoin.

* * * * *